United States Patent

Baumann et al.

[11] Patent Number: 4,567,170
[45] Date of Patent: Jan. 28, 1986

[54] 3-CHLORO-3-PHENYLPROP-2-ENYL THIOPHOSPHATES AND THEIR USE FOR CONTROLLING PESTS

[75] Inventors: Annegrit Baumann, Mannheim; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 550,025

[22] Filed: Nov. 8, 1983

[30] Foreign Application Priority Data

Nov. 16, 1982 [DE] Fed. Rep. of Germany ....... 3242281

[51] Int. Cl.⁴ .................. C07F 9/165; A01N 57/14
[52] U.S. Cl. .................... 514/128; 514/130; 514/134; 514/136; 260/949; 260/951; 260/956
[58] Field of Search ............. 260/956, 951, 949, 906; 514/128, 130, 136, 134

[56] References Cited

U.S. PATENT DOCUMENTS 3,662,034  5/1972  Oswald et al. ............ 260/956
3,903,209  9/1975  Stolzer et al. ............ 260/956

FOREIGN PATENT DOCUMENTS 3242281  5/1984  Fed. Rep. of Germany .

Primary Examiner—Anton H. Sutto
Attorney, Agent, or Firm—Keil & Weinkauf

[57] ABSTRACT

Thiophosphates of the formula I

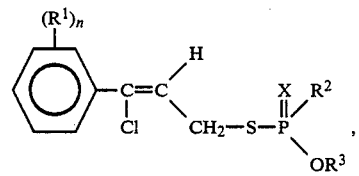

where $R^1$ is hydrogen, or not more than 4 identical or different substituents $R^1$ may be present, each of which is fluorine, chlorine or bromine, straight-chain or branched alkyl of not more than 5 carbon atoms, alkoxy of not more than 3 carbon atoms or alkylthio of not more than 3 carbon atoms, $R^2$ is alkoxy, alkylthio or alkylamino, each of which is substituted by straight-chain or branched alkyl of not more than 5 carbon atoms, $R^3$ is alkyl of not more than 3 carbon atoms and X is oxygen or sulfur, a process for their preparation and their use as pesticides.

3 Claims, No Drawings

3-CHLORO-3-PHENYLPROP-2-ENYL THIOPHOSPHATES AND THEIR USE FOR CONTROLLING PESTS

The present invention relates to 3-chloro-3-phenyl-prop-2-enyl thiophosphates whose action is preferentially insecticidal and acaricidal, a process for their preparation and their use for controlling insects and spider mites.

Olefinically unsaturated phosphoric acid esters containing halogens and phenol ester groups are disclosed in, for example, German Laid-Open Application DOS Nos. 1,567,092, DOS 2,411,809 and DOS 2,834,505.

We have found that 3-chloro-3-phenylprop-2-enyl thiophosphates of the formula I

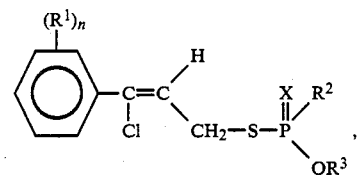

where $R^1$ is hydrogen, or not more than 4 identical or different substituents $R^1$ may be present, each of which is fluorine, chlorine or bromine, straight-chain or branched alkyl of not more than 5 carbon atoms, alkoxy of not more than 3 carbon atoms or alkylthio of not more than 3 carbon atoms, $R^2$ is alkoxy, alkylthio or alkylamino, each of which is substituted by straight-chain or branched alkyl of not more than 5 carbon atoms, $R^3$ is alkyl of not more than 3 carbon atoms and X is oxygen or sulfur, have a particularly high insecticidal, preferably acaricidal, activity and are superior to the conventional, similar active ingredients which are themselves highly effective.

The precursors of the novel phosphates can be prepared as described in J. Chem. Soc. C 1970, page 2484 and Ber. 98 (1965), 3554; the reactions according to equations (1) to (3) below give the required precursor (II), and can be carried out in industrial processes, using conventional equipment. The reaction of the precursor (II), which is a 1-phenyl-1,3-dichloropropene, with a (conventional) thio- or dithiophosphate salt (III) gives the active ingredient (I)

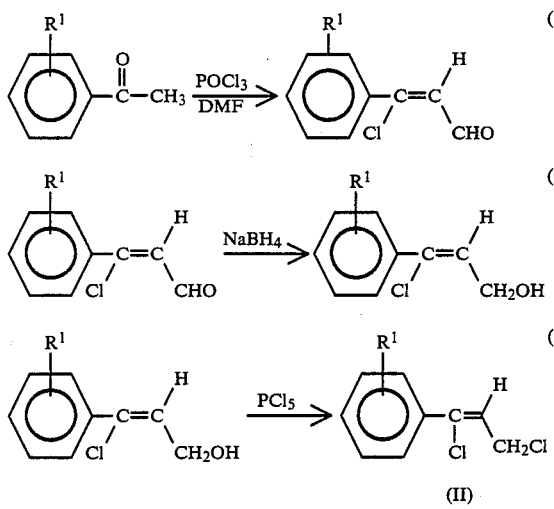

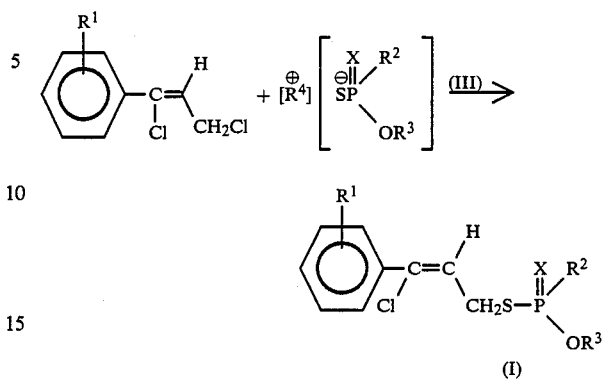

The salts of the formula III are known compounds, and their preparation is described in, for example, Houben-Weyl, Methoden der organischen Chemie, 4th edition, volume 12/2, page 690.

Suitable cations for these salts, in addition to the ammonium ion, are substituted ammonium ions, eg. dimethylammonium or diethylammonium ions, or alkali metal ions, eg. Na or K.

The reactions are carried out in a conventional solvent, for example an aliphatic or aromatic hydrocarbon, chlorohydrogen or nitrohydrocarbon, such as benzene, toluene, xylene, chlorobenzene, chloroform, methylene chloride or carbon tetrachloride, a cyclic or acyclic ether, such as tetrahydrofuran or diethyl ether, a ketone, such as acetone or cyclohexanone, or a nitrile, such as acetonitrile. Mixtures may also be used. In some cases, it is advisable to carry out the reaction in a two-phase system, using water and a water-immiscible solvent, eg. xylene, toluene or methyl-t-butyl ether, if necessary with the addition of a phase-transfer catalyst, such as a crown ether or a quaternary ammonium salt.

An adequate reaction velocity is generally achieved at below 100° C., preferably at from 40° to 60° C.; the boiling point of the solvent may limit the temperature.

The methods of preparation below relate to precursors of the novel active ingredients.

Preparation method A

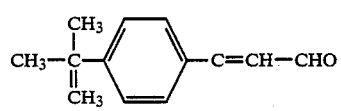

59 ml of dimethylformamide were added dropwise to 59 g (0.38 mole) of phosphoryl chloride at from 20° to 30° C. in the course of 30 minutes. The mixture was cooled to −5° to +5° C., after which 51.8 g (0.29 mole) of 4-tert.-butylacetophenone were added dropwise. When the cooling bath was removed, the temperature increased to 55°–60° C., and the mixture was stirred for a further 3 hours at this temperature and was then poured onto ice. The product was extracted by shaking with methylene chloride, the organic phase was washed with 10% strength sodium bicarbonate solution, dried and evaporated down, and 61.2 g of a viscous oil ($n_D^{25}$: 1.5878) were obtained.

Preparation method B 60.3 g (0.27 mole) of the product of preparation method A were dissolved in 350 ml of ethylene glycol dimethyl ether, and a solution of 5.15 g (0.135 mole) of sodium borohydride in 100 ml of water was added at from 20° to 30° C., after which stirring was continued for 1 hour at room temperature, the mixture was acidified with 10% strength sulfuric acid and evaporated down under reduced pressure, the residue was treated with methyl tert.-butyl ether and water, and the organic phase was evaporated down to give 54.6 g of an oil ($n_D^{25}$: 1.5640).

Preparation method C 54.5 g (0.24 mole) of the product of preparation method B were dissolved in 150 ml of absolute chloroform, a few drops of dimethylformamide were added and 41.6 g (0.35 mole) of thionyl chloride were added dropwise at room temperature. Thereafter, stirring was continued for 1 hour at room temperature and for 2 hours at 50° C., and the mixture was evaporated down under reduced pressure to give 58.3 g of a virtually colorless liquid ($n_D^{23}$: 1.5700).

The Examples which follow illustrate the preparation of the novel active ingredients.

PREPARATION EXAMPLE 1

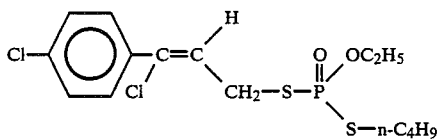

11.1 g (0.05 mole) of 1-(p-chlorophenyl)-1-chloro-3-chloroprop-1-ene in 100 ml of absolute acetonitrile were initially taken at room temperature and 13.6 g (0.0525 mole) of dimethylammonium O-ethyl-S-n-butyldithiophosphate, likewise dissolved in acetonitrile, were added gradually. The mixture was stirred for 8 hours at from 40° to 50° C., treated at room temperature with 5% strength sodium bicarbonate solution and evaporated down, the residue was taken up in ether, the solution was extracted by shaking 3 times with water, and the organic phase was dried, filtered and evaporated down. 17.8 g (89% of theory) of a yellowish oil were obtained. The compound is listed as number 14 in Table 1 below.

$n_D^{25} = 1.5851$

| Analysis:  | C     | H   | S     | Cl    | P    | O    |
|------------|-------|-----|-------|-------|------|------|
| calculated | 45.12 | 5.3 | 16.06 | 17.76 | 7.76 | 8.01 |
| found      | 45.4  | 5.3 | 16.0  | 16.0  | 18.3 | 7.5  |

PREPARATION EXAMPLE 2

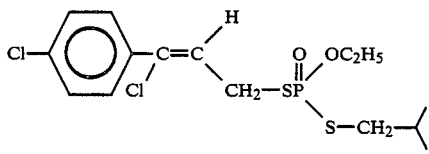

The procedure described above was followed, using 11.1 g (0.05 mole) of 1-(p-chlorophenyl)-1-chloro-3-chloroprop-1-ene and 13.6 g (0.0525 mole) of dimethylammonium O-ethyl-S-sec-butyldithiophosphate. Yield: 16.8 g (84% of theory) of a yellow oil.

After purification over a silica gel column (mobile phase: 8:1 mixture of n-hexane with acetone), 12.1 g of the desired compound were obtained. The compound is listed as number 10 in the Table below.

$n_D^{25} = 1.5841$

TABLE 1

| Analysis:  | C     | H   | S     | Cl    | P    | O    |
|------------|-------|-----|-------|-------|------|------|
| calculated | 45.12 | 5.3 | 16.06 | 17.76 | 7.76 | 8.01 |
| found      | 45.5  | 5.3 | 15.9  | 18.4  | 7.1  |      |

Among the compounds below, those for which physical data are given have been prepared, compounds for which no data are given are expected to have a similar action because of the structural similarity.

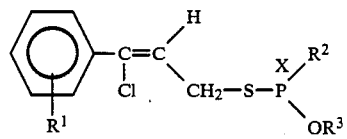

| R¹         | X | R²                                 | R³      | $n_D^{25}$ |
|------------|---|------------------------------------|---------|--------|
| H          | O | sec-C₄H₉S—                         | C₂H₅    | 1.5741 |
| H          | O | n-C₃H₇S—                           | C₂H₅    | 1.5813 |
| H          | O | i-C₄H₉S—                           | C₂H₅    | 1.5743 |
| H          | O | i-C₃H₇S—                           | C₂H₅    | 1.5802 |
| H          | O | n-C₅H₁₁S—                          | C₂H₅    | 1.5702 |
| H          | O | i-C₅H₁₁S—                          | C₂H₅    | 1.5690 |
| H          | O | n-C₄H₉S—                           | C₂H₅    | 1.5766 |
| 4-Cl       | O | sec-C₄H₉S—                         | C₂H₅    | 1.5844 |
| 4-Cl       | O | n-C₃H₇S—                           | C₂H₅    | 1.5918 |
| 4-Cl       | O | i-C₄H₉S—                           | C₂H₅    | 1.5841 |
| 4-Cl       | O | i-C₃H₇S—                           | C₂H₅    | 1.5897 |
| 4-Cl       | O | n-C₅H₁₁S—                          | C₂H₅    | 1.5767 |
| 4-Cl       | O | i-C₅H₁₁S—                          | C₂H₅    | 1.5753 |
| 4-Cl       | O | n-C₄H₉S—                           | C₂H₅    | 1.5851 |
| 4-Cl       | S | C₂H₅O—                             | C₂H₅    |        |
| 4-CH₃—     | O | n-C₃H₇S—                           | C₂H₅    | 1.5788 |
| 4-CH₃—     | O | i-C₃H₇NH—                          | C₂H₅    | 1.5602 |
| 4-t-C₄H₉—  | S | C₂H₅O—                             | C₂H₅    | 1.5710 |
| 4-t-C₄H₉—  | S | CH₃O—                              | CH₃     |        |
| 4-t-C₄H₉—  | O | n-C₃H₇S—                           | C₂H₅    | 1.5683 |
| 4-t-C₄H₉—  | O | i-C₃H₇NH—                          | C₂H₅    | 1.5605 |
| 4-CH₃O—    | S | C₂H₅O—                             | C₂H₅    |        |
| 4-CH₃O—    | O | n-C₃H₇S—                           | C₂H₅    | 1.5850 |
| 4-CH₃O—    | O | i-C₃H₇NH—                          | C₂H₅    | 1.5690 |
| 4-t-C₄H₉—  | O | C₂H₅O—                             | C₂H₅    | 1.5457 |
| 3-Br, 4-F  | S | C₂H₅O—                             | C₂H₅    | 1.5900 |
| 3-Br, 4-F  | O | n-C₃H₇S—                           | C₂H₅    | 1.5880 |
| 3-Br, 4-F  | O | i-C₃H₇NH                           | C₂H₅    | 1.5720 |
| 3,4-CH₃    | S | C₂H₅O—                             | C₂H₅    |        |
| 3,4-CH₃    | O | n-C₃H₇S—                           | C₂H₅    |        |
| 3,4-Cl     | S | C₂H₅O—                             | C₂H₅    | 1.6015 |
| 3,4-Cl     | O | n-C₃H₇S—                           | C₂H₅    | 1.5997 |
| 4-CH₃S—    | S | C₂H₅O—                             | C₂H₅    |        |
| 4-CH₃S—    | O | n-C₃H₇S—                           | C₂H₅    |        |
| 3,4-Cl     | O | C₂H₅O—                             | C₂H₅    | 1.5748 |
| 3,4-Cl     | O | i-C₃H₇NH—                          | C₂H₅    | 1.5838 |

The abovementioned (and other) active ingredients according to the invention are applied in the usual manner for phosphates. Details on formulation, action and suitable mixture components for achieving synergistic and other advantageous effects are given for instance in U.S. Pat. No. 4,320,122, which is incorporated herein by reference.

To demonstrate the effectiveness of the active ingredients according to the invention, the experiments described below were carried out; the compound used for comparison purposes was the commercial product chlorphenvinphos, which is known to be effective;

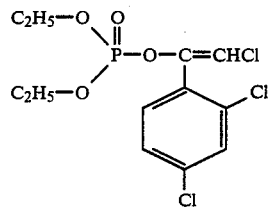

Breeding experiment with housefly larvae (*Musca domestica*)

4.5 ml of skimmed milk was filled into 50 ml penicillin flasks, and 0.5 ml of the aqueous active ingredient formulation was added. After brief mixing, a ball of absorbent cotton was introduced and approx. 50 egg larvae of the housefly were placed on it.

The flasks were covered and stored at room temperature, and developments were assessed after 7 days.

In this experiment, active ingredients nos. 1, 2, 3, 4, 7, 9 and 10 in the Table, at concentrations of 2.5 to 10 ppm (in the aqueous solution), achieved kill rates of up to 100%.

Action on spider mites (*Tetranychus telarius* (Test A)

Potted bush beans which had developed the first pair of true leaves and were under heavy attack from spider mites (*Tetranychus telarius*) of all stages were sprayed to runoff from all sides in a spray cabinet with aqueous formulations of the active ingredients.

The plants were placed on a rotatable disc and were sprayed with 50 ml of spray liquor. Spraying lasted for about 22 seconds. The plants were investigated after 8 days for living spider mites.

In this experiment, active ingredients nos. 1, 2, 3, 7, 8, 9 and 10 in the Table achieved 100% kill at a concentration of 0.02% and less; the comparative agent was at best only half as effective.

Action on spider mites (*Tetranychus telarius*)

Test B—residual action

Potted bush beans which had developed the first pair of true leaves were sprayed to runoff in a spray cabinet with aqueous formulations of the active ingredients. The plants were placed on a rotatable disc and were sprayed from all sides with 50 ml of spray liquor. Spraying lasted for about 20 seconds.

After 24 hours infected pieces of leaves with at least 100 spider mites of all stages on them were placed on the plants.

The extent to which the plants had been attacked was assessed after 8 days.

In this experiment, compounds nos. 1, 2, 3, 4, 7, 9 and 14 in the Table achieved full kill at a concentration of 0.05% or less; the comparative agent was, as in the foregoing experiment, only half as effective at best.

Contact action on mosquito larvae (*Aedes aegypti*)

Active ingredient formulations were added to 200 ml of tapwater, and 30 to 40 mosquito larvae in the 4th stage were introduced.

The temperature was kept at 20° C. The action was assessed after 24 hours.

In this experiment, all compounds in the Table down to no. 14 were used; at concentrations of from 0.02 to 0.25 ppm, they had an action which was up to 5 times stronger than that of the comparative agent.

Contact action and effect of ingested food on caterpillars of the diamondback moth (*Plutella maculipennis*)

Leaves of young cabbage plants were dipped for 3 seconds in aqueous emulsions of the active ingredients, and, after excess liquid had been briefly allowed to drip off, were placed on a moist filter paper in a Petri dish. 10 caterpillars in the 4th stage were then placed on the leaves. The action was assessed after 48 hours.

In this experiment, active ingredients nos. 1, 2, 3, 8, 9, 10 and 14 in the Table were fully effective at concentrations of 0.02% or less.

Contact action on bulb eelworms (*Ditylenchus dipsaci*)

50 to 100 active nematodes were added to 1 ml of water, and introduced into 10 ml penicillin flasks. 1 ml of the aqueous active ingredient formulations was then added.

After 24 hours the activity of the nematodes was assessed under the microscope.

In this experiment, an approx. 90% kill was achieved in all instances with compounds nos. 1, 2, 3, 4, 7, 8, 10, 11, 12 and 14; the concentration in each case was 10 ppm.

We claim:

1. A thiophosphate of the formula

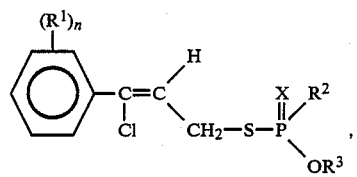

where $R^1$ is hydrogen, or not more than 4 identical or different substituents $R^1$ may be present, each of which is fluorine, chlorine or bromine, straight-chain or branched alkyl of not more than 5 carbon atoms, alkoxy of not more than 3 carbon atoms or alkylthio of not more than 3 carbon atoms, $R^2$ is alkoxy, alkylthio or alkylamino, each of which is substituted by straight-chain or branched alkyl of not more than 5 carbon atoms, $R^3$ is alkyl of not more than 3 carbon atoms and X is oxygen or sulfur.

2. A pesticide containing inert additives and an effective amount of 3-chloro-3-phenylprop-2-enylthiophosphate of the formula I as defined in claim 1.

3. A process for combatting pests, wherein an effective amount of 3-chloro-3-phenylprop-2-enylthiophosphate of the formula I as defined in claim 1 is allowed to act on the pests and/or their habitat.

* * * * *